US005356521A

United States Patent [19]

Nekoksa et al.

[11] Patent Number: 5,356,521
[45] Date of Patent: Oct. 18, 1994

[54] PROCESS FOR MONITORING BIOFILM ACTIVITY

[75] Inventors: George Nekoksa, San Ramon; George J. Licina, Campbell, both of Calif.

[73] Assignee: Electric Power Research Institute, Inc., Palo Alto, Calif.

[21] Appl. No.: 48,603

[22] Filed: Apr. 16, 1993

Related U.S. Application Data

[62] Division of Ser. No. 771,701, Oct. 4, 1991, Pat. No. 5,246,560.

[51] Int. Cl.⁵ .............................................. G01N 27/26
[52] U.S. Cl. ............................ 204/153.12; 204/153.1; 204/153.11
[58] Field of Search ................... 204/153.11, 153.12, 204/153.1, 404, 400

[56] References Cited

U.S. PATENT DOCUMENTS 3,331,021 7/1967 Marsh et al. ...................... 204/404
3,661,750 5/1972 Wilson .................................. 204/404

Primary Examiner—John Niebling
Assistant Examiner—Bruce F. Bell
Attorney, Agent, or Firm—Laurence Coit

[57] ABSTRACT

Disclosed is a novel electrochemical probe and technique to monitor biofilm activity before the biofilm has been permanently established and microbiologically influenced corrosion (MIC) initiated. This probe includes two sets of metal electrodes isolated from each other. A power source is used to apply a potential difference of between 50 and 500 mV on the two sets of electrodes to activate the probe. Programmed timing, measuring and switching equipment and a data recording device monitors the biofilm-caused depolarization effects on the electrode sets by measuring an increase of DC current produced by the applied potential difference. The equipment also monitors DC current generated between the electrodes after removing the power source and records the AC resistance between the electrodes indicating mostly the resistance of the biofilm covering the electrodes.

8 Claims, 5 Drawing Sheets

PROCESS FOR MONITORING BIOFILM ACTIVITY

This is a division of application Ser. No. 07/771,701 filed Oct. 4, 1991, now U.S. Pat. No. 5,246,560.

BACKGROUND OF THE INVENTION

1. Field of Invention

This invention relates to monitoring biological activity and growth on objects in contact with aqueous solutions. More specifically, the invention relates to measuring the activity and growth of bacterial films on the surfaces of pipes and equipment containing or transporting water.

2. Description of the Related Art

Many surfaces immersed in water or a substance containing water will soon be coated with a biological growth. The process starts with adsorption of organic material and continues through colonization of bacteria, development of bacterial or algal slime films to the growth of various plants and animals. The development rate can be especially fast in seawater where the first film covering is completed in about two hours and a complete bacterial slime film is formed between 24 and 48 hours after first immersion. (*Metals Handbook, Ninth Edition*, Vol. 13, pages 900–901, ASM International 1987).

Uncontrolled biological growth increases the resistance of flow through conduits, pipes, heat exchangers, and condensers; and will ultimately block the passageway completely. Restriction of flow generally reduces the capacity of the process using the water. Complete blockage of flow requires costly down time to clean the structure. In addition, biological growth accelerates corrosion of the structure through the mechanisms of microbiolocally influenced corrosion (MIC).

Methods have been used to slow MIC and biological growth in water systems. One approach has been to coat the exposed surfaces of the structure with a biocide bearing or anti-fouling material. Paints containing cuprous oxide or organo-tin are the most common type of anti-fouling coating. A significant drawback to the coating approach is that periodically the coatings must be renewed after the toxic elements leach into the water stream or are otherwise dissolved. The toxicity of the coatings has prompted many of them to be banned. Another problem with this approach is that coatings must be meticulously applied under controlled environment or the coating will peel off in the harsh environment of turbulent flow, thus leaving the structure unprotected against further growth and electrochemical corrosion. Replacement of coatings involves substantial labor for cleaning and preparing the surface and applying the coating. Unless there are back-up systems, coating of critical piping and components result in expensive plant downtime. In critical systems such as emergency cooling water systems in nuclear power plants, coatings are disfavored because of the risk that improperly applied coatings may come off in sheets thus plugging the cooling water source during an emergency.

A commonly used approach to controlling biological growth is to inject a biocide such as chlorine or ozone into the water to kill the bacteria. Since chlorine has a detrimental effect on the environment, strict federal regulations limit the amount of chlorine which can be injected. Thus, it is vitally important to inject chlorine only when necessary. In present piping systems, there is no practical way to inspect or monitor biological activity and growth. Consequently, chlorine is injected sufficiently frequently and in sufficient amounts to insure a clean system. However, the amount of chlorine required to control biological growth varies considerably based on the layout of the equipment, the location of injection points and seasonal changes in bacteria growth rates. Therefore, the biocide injection approach usually results in overdosing which has an adverse impact on the environment and system operating costs. In some cases, expensive dechlorination systems have been added at cooling water discharges to allow high levels of chlorine dosage at critical components and still meet chlorine discharge regulations. To eliminate this problem, an effective method of monitoring biofilm activity and growth is needed so that chlorine injection can be limited to that amount and that periodicity which is effective in preventing the build up of biological growth.

The existing technology to monitor biofilm activity in plants requires exposure of rectangular or small button coupons to the environment of concern, removal of the coupons for inspection, and bacteria cultivation or enzyme analyses. This technology is time consuming and does not provide information fast enough, for instance, to adjust the chlorinators before the biofilm gets established and becomes resistant to chlorine. Other existing methods monitor biofouling in the tubes by heat transfer loss, increase of the water pressure loss or decrease of flow through the tubes. However, these systems indicate biofouling only after a significant buildup. As M. Bibb noted in her article "Bacterial Corrosion," Corrosion and Coatings South Africa, October, 1984, "Once the organism is established beneath the tuberculous crust, huge concentrations of chlorine are required to penetrate this crust." Thus, remedial action under these conditions involves substantial release of chlorine to the environment as opposed to that required when the biofilm is a thin layer.

An existing electrochemical corrosion rate meter is described in U.S. Pat. No. 3,661,750. Electrochemical corrosion probes are shown in U.S. Pat. Nos. 3,633,099 and 3,639,876. A liquid water sensor useful for indicating a corrosive condition in natural gas pipelines is described in U.S. Pat. No. 4,506,540. All the existing electrochemical methods measure data related to corrosion. Electrochemical methods, such as linear polarization, corrosion potential monitoring, polarization testing to determine pitting and repassivation potentials, and AC impedance spectroscopy, have been used with success for monitoring of general corrosion and an indication of pitting corrosion in the plants. These electrochemical methods are not sensitive enough to determine biofilm activity; the instrumentation is complex and expensive, and the data analysis is complicated. The existing monitoring technologies are not practical nor sensitive enough to provide online monitoring of active biofilm formation and MIC in a plant.

Enzyme electrodes, used for instance to measure concentration of glucose in blood or urine, use electrochemical probes with porous graphite/platinum/enzyme electrodes polarized by 325 to 650 mV. The enzyme electrodes operate as amperometric sensors; that is a higher concentration of glucose is indicated by higher DC current flow. An enzyme probe is described in U.S. Pat. No. 4,970,145. The enzyme probe is not sensitive to biofilm activity in a plant and does not work in flowing water applications.

SUMMARY OF THE INVENTION WITH OBJECTS

It is one object of the present invention to provide an apparatus and method for monitoring the activity and growth of biofilms in aqueous environments.

It is another object of the invention to provide a biofilm monitoring system which can differentiate variations in the DC polarization characteristics from changes in ohmic resistance due to a biofilm or other deposit.

It is another object of the invention to provide an effective monitoring system for biofilm activity and growth which can be used in the control of anti-fouling systems.

It is still another object of the invention to minimize costs associated with monitoring and controlling MIC and biological fouling and to reduce the resulting plant downtime.

It is yet another object of the invention to minimize environmental degradation caused by the excessive use of biocides.

These and other objects are accomplished with a novel electrochemical probe and technique to monitor biofilm activity before the biofilm has been permanently established and MIC initiated. This probe includes two sets of metal electrodes isolated from each other. A power source is used to apply a potential difference of between 50 and 500 mV on the two sets of electrodes to activate the probe. All electrode potentials are imposed and measured between the two identical electrodes; thus they are unaffected by the potential of the pipe work or by changes in the corrosion potential that may accompany exposure of the probe. The closely spaced metal electrodes eliminate IR drop in the water during application of applied potentials and permit a determination of the AC resistance of biofilm, effectively independent of the resistivity of the water. Programmed timing, measuring and switching equipment and a data recording device monitor the biofilm-caused depolarization effects on the electrode sets by measuring an increase of DC current produced by the applied potential difference. The equipment also monitors DC current generated between the electrodes after removing the power source and records the AC resistance between the electrodes indicating mostly the resistance of the biofilm covering the electrodes.

Pre-programmed timing and switching equipment ensures an optimum test sequence. The following is an example of a test sequence: Probe terminals are shorted for 23½ hours; at the end of this period, any DC current generated by the probe is measured for instance by inserting an ammeter between probe terminals; then a power source with a preset DC potential of, for example, 200 mV is connected to the probe terminals for 30 minutes. At the end of this period, the DC applied current is measured and the probe terminals are once more shorted for 23½ hours. This sequence is then repeated.

DETAILED DESCRIPTION OF THE INVENTION

Figure 1A:
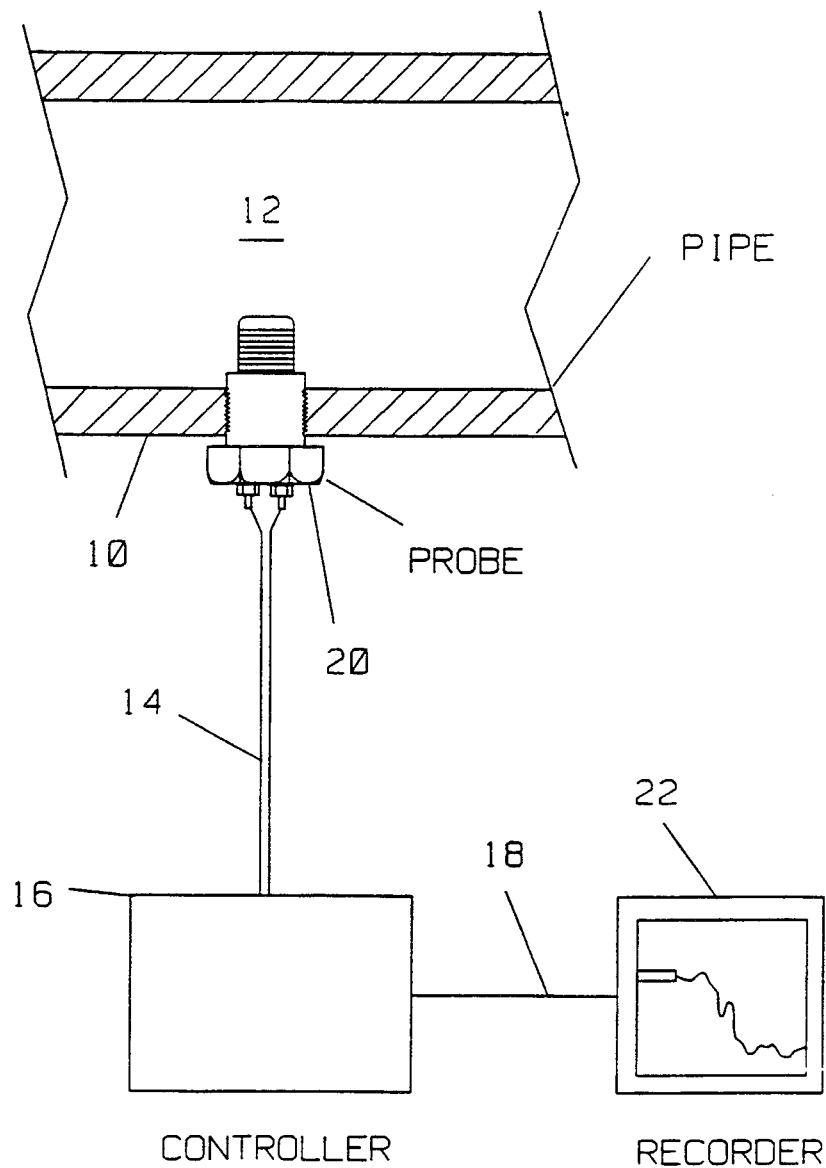
FIG. 1A is a schematic diagram of the biofilm monitoring system.

The basis of the present invention is a biofilm activity sensing probe and monitoring technique consisting of activating the probe by applying a potential between two metal electrode sets and monitoring the current required to achieve that potential and the current generated by the probe after removing the power source. This probe can also be used to monitor resistance of the biofilm on the surface of the electrodes using an existing AC resistance meter. Referring to FIG. 1A, a schematic diagram for the biofilm monitoring system is shown. The system is shown connected to a pipe 10 transporting water 12. Although the system is depicted connected to a pipe, it is equally applicable to other conduits, tanks, pumps, heat exchangers and condensers. Probe 20 is inserted via threaded connection into pipe 10 so that the electrodes of probe 20 are immersed. For high pressure applications, the probe 20 may be installed in high pressure fittings that are welded to pipe 10 or mounted on a flange (not shown) which is welded or bolted to an off sticker (not shown) provided the electrodes of probe 20 extend into the water. Probe 20 is electrically connected to controller 16 by conductors 14. Controller 16 contains a DC voltage source, a DC current meter and an AC impedance meter as are commonly known in the instrumentation arts. Also included in controller 16 is a sequencer which automatically applies DC voltage to the probe 20 and reads current flow applied to the probe and current or voltage generated by the probe in accordance with the sequence described hereinbelow. Controller 16 is electrically connected to recorder 22 via conductor 18. Recorder 22 prints a strip chart indicating the time history of biofilm activity and buildup. Alternately, the output of controller 16 could be directed to an indicator or data logging system. In addition to recording or indicating biofilm status, the controller 16 output can be used to automate a biofilm control system.

Figure 1B:
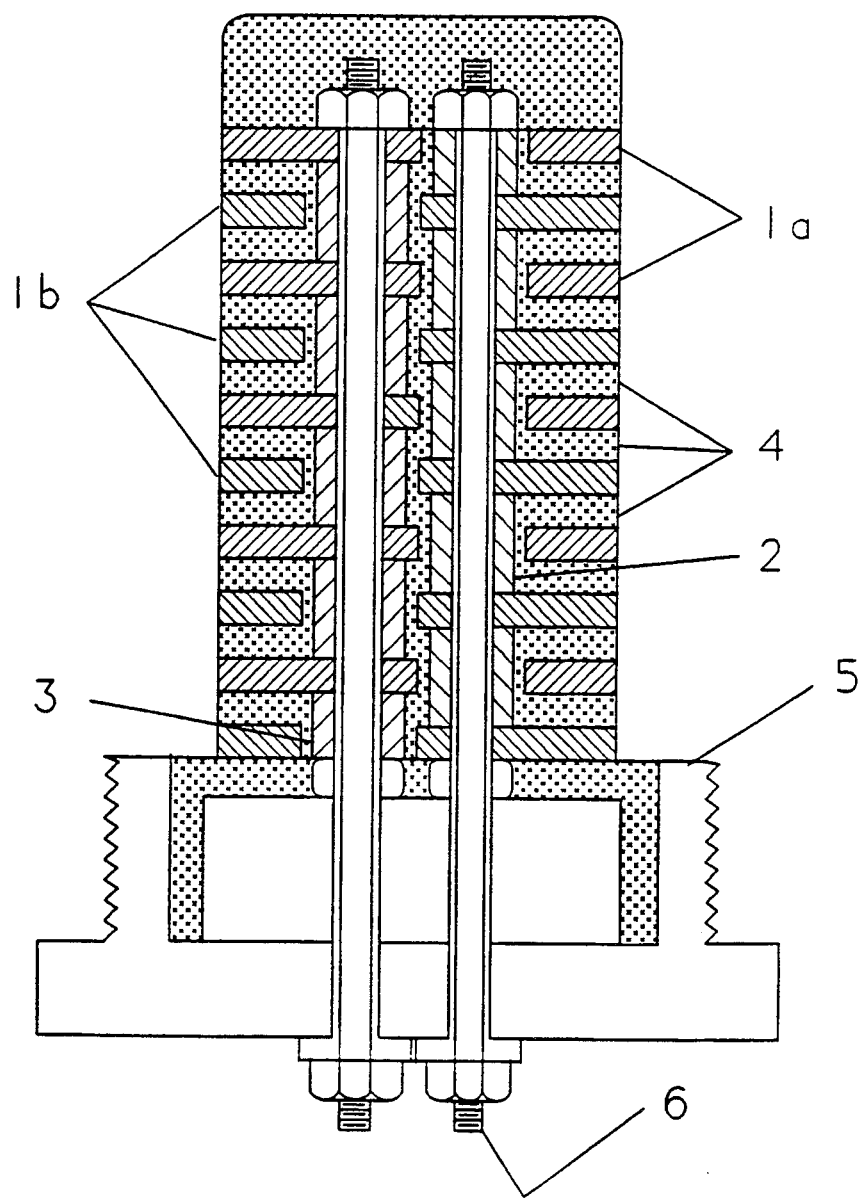
FIG. 1B is a sectional, elevation view of the biofilm probe.
Figure 2A:
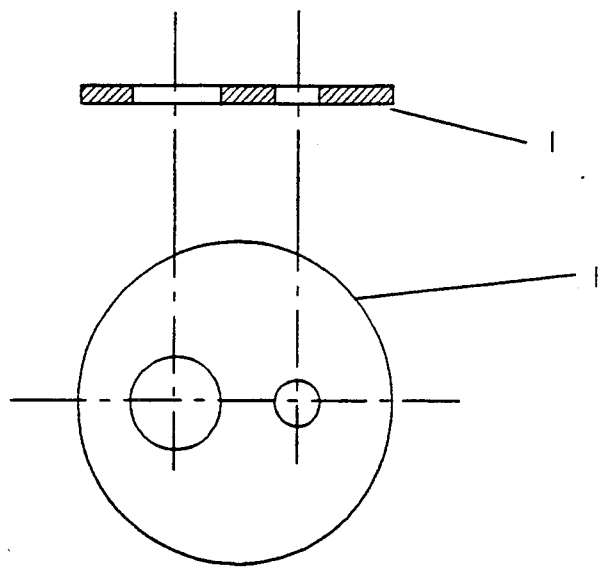
FIGS. 2a and 2b is a detail of the biofilm probe components.
Figure 2B:
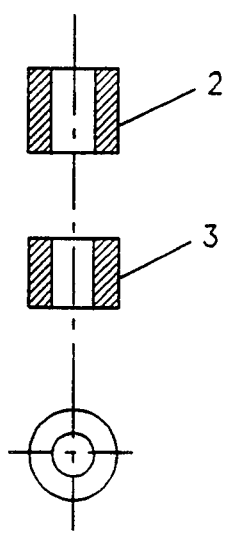

Turning now to FIGS. 1B, 2a and 2b, details of probe 20 are shown. Two sets of metal discs 1a and 1b, each with two holes of different diameter in each disc, and metal rings 2, 3 are assembled on two metal threaded rods 6 with washers and nuts so that each rod is electrically common with one set of discs and insulated from the other. This assembly is then installed into or onto a probe plug 5 and the contacts between metal components are sealed with epoxy 4 or an another insulating material suitable for immersion in an aqueous solution. The probe 20 thus formed consists of two, electrically insulated electrodes made from identical materials. The discs 1a, 1b, metal rings 2, 3 and rods 6 can be formed from any metallic conductor. However, biofilm activity has greater affect on tile electrochemical properties of passivating metals such as stainless steels. Stainless steel, specifically AISI Type 304, has been found to be acceptable for the electrodes. Other materials, for example, titanium, carbon steel, or copper alloys, may also be used for electrodes since their surfaces and associated electrochemical reactions may be affected by biofilms.

In this two-electrode electrochemical probe, each electrode is represented by one set of discs 1a and 1b exposed to the electrolyte to be tested. Since the electrodes are made of identical material and are insulated from the pipe or structure, the potentials measured or impressed between the two electrodes are not affected by the corrosion potential, or changes in the potential of the piping system in relation to ground potential. The diameters of metal discs 1a, 1b and epoxy 4 are consistent and coincide so that the exterior surface of probe 20 is uniformly cylindrical. In this manner, a biofilm coating on the exterior surface of probe 20 constitutes the most direct, conductive path between discs 1a of one electrode and discs 1b of the other electrode. The ends of the two rods 6 penetrating the plug 5 represent terminals for potential application and current monitoring by controller 16.

Probe 20 mimics the condition on passivating metals (mostly stainless steels) exposed to cooling water where biological activity and MIC occur preferentially at welds, crevices or inclusions; that is, in locations with potential differences caused by differences in metal, metal surface quality, surface film and electrolyte. Current flows can not be readily measured on the structure. However, the probe 20 develops a current flow which can be readily measured. The potential difference applied to the electrodes of probe 20 provides a condition that is readily amenable to the establishment of biofilm and to measurements of currents and potentials. Biofilm formation enhances the electrochemical reactions on the surface of the electrodes thereby providing an indication of increased biofilm activity. Similarly, the application of a constant DC potential difference between the electrode sets of the probe produces a current flow simulating the above condition on stainless steels. The applied DC current encourages different biofilm conditions on each electrode. An active biofilm is indicated by an increase of the applied DC current between the electrodes caused by the biofilm depolarization effect on the cathodic electrode. Very small applied potentials on the electrodes would have only insignificant effects on the biofilm; potentials between 50 to 500 mV would mimic potential differences at welds, crevices and inclusions; while larger potentials would impede biofilm growth and could cause corrosion of the electrodes. Therefore, a selection of the applied potential between the electrodes and duration over which potential is applied can produce a probe with fast or slow development of active biofilm. In most practical applications, potentials between 150 and 300 mV applied for 10 to 60 minutes per day would produce active biofilm on the probe before it can be seen on the plant component.

The electrode set with an active biofilm requires higher polarization current to maintain the potential difference between the electrode sets. The increase of the applied current is an indication of the biofilm activity and resulting electrode depolarization.

After removal of the power source, the electrode set with an active biofilm becomes more noble than the other electrode set. The potential difference between the electrode sets generates a DC current flow of the same sense as that from the removed power source. This generated current is an excellent indicator of the biofilm activity.

Evaluation of all three techniques, that is, an increase in applied current, an increase in the generated current, and changes in AC resistance, provides the best indication of biofilm activity and deposition. However, each technique alone, or a combination of any two, should also provide a satisfactory indicator of biofilm activity in most environments.

Figure 3:
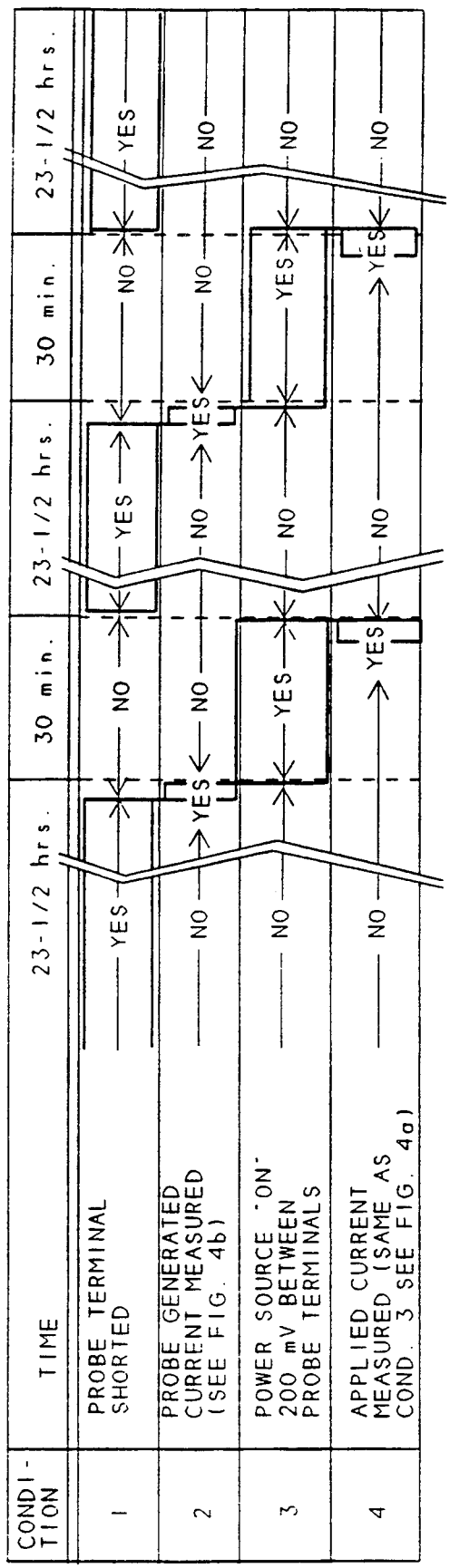
FIG. 3 shows an example of the biofilm monitoring system test sequence.
Figure 4A:
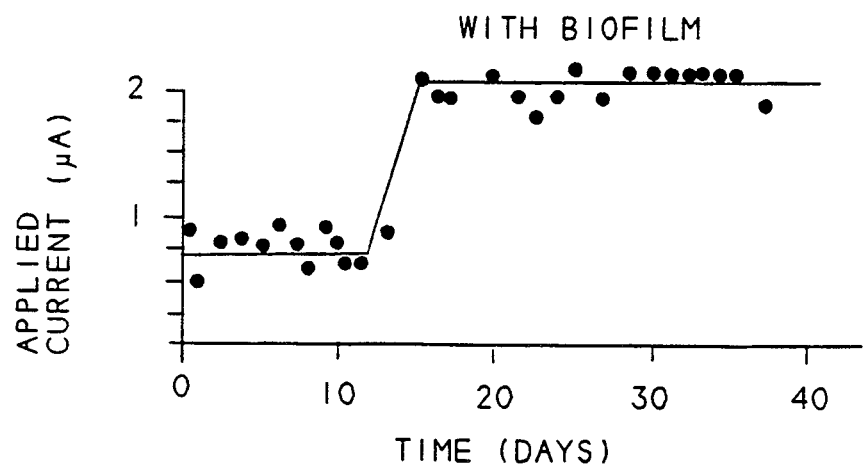
FIG. 4a shows a graph of applied DC current and FIG. 4b shows a generated DC current versus time. An increase of applied and generated currents indicates biofilm activity increase.
Figure 4B:
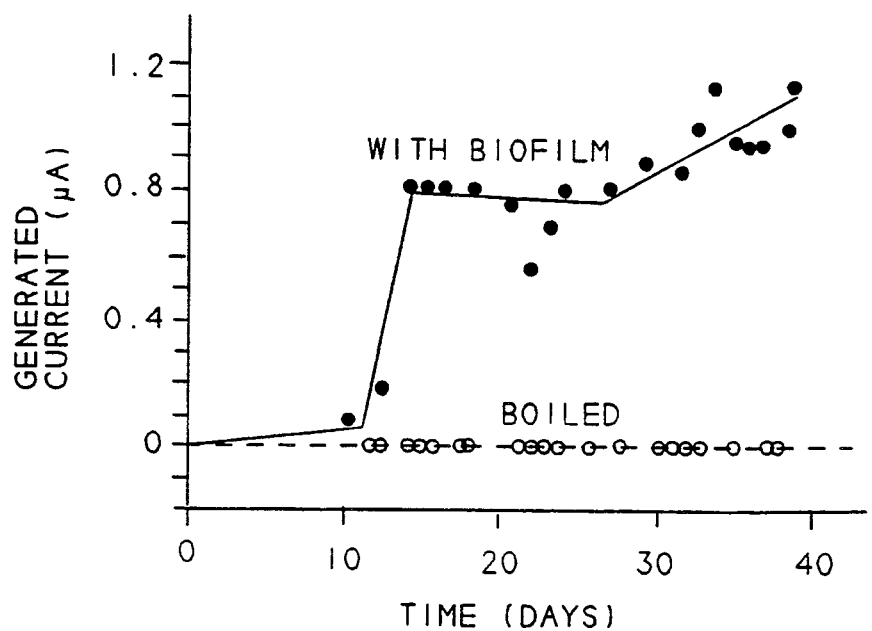

An example of the monitoring sequence is shown in FIG. 3. After installation of the probe in a pipe or tank, the probe terminals were shorted for 23½ hrs. (see condition 1). At the end of this period, the terminals were shunted through a shunt and the probe generated current was measured (see condition 2). After the generated current measurement, 200 mV were applied from a DC power source between the probe terminals for 30 min. (see condition 3). At the end of the potential application, the resulting polarization current was measured (see condition 4), then the power source was removed and the terminals were once more shorted (see condition 1). This test sequence was repeated every day and the recorded measurements of applied and generated currents were plotted into graphs as is shown in FIGS. 4a and 4b.

In a laboratory test, an increase of both currents indicated the start and/or increase of the biofilm activity. In a plant application, such an increase of the monitored currents can be used as an indication that chlorination or pipe cleaning is required

We claim:

1. A process for monitoring biofilm activity on a structure exposed to an aqueous solution comprising the steps of:
    a. submerging two electrodes made from the same electrically conducting material, in said aqueous solution and electrically insulating said electrodes from one another and said structure;
    b. measuring the electrical characteristics of said two electrodes;
    c. measuring the current flow through said electrodes after connecting said electrodes to a power supply;
    d. determining biofilm activity on said electrodes by analysis of said electrical current generated or said electrical current flow;
    whereby changes in said electrical current generated or said electrical current flow indicate biofilm activity on said electrodes.

2. A process for monitoring biofilm activity on a structure exposed to an aqueous solution as recited in claim 1 wherein the step of connecting said electrodes to a power source further comprises applying a DC potential on said electrodes.

3. A process for monitoring biofilm activity on a structure exposed to an aqueous solution as recited in claim 2 further comprising applying a DC potential on said electrodes for an extended period of time and, removing said applied DC potential before measuring the electrical current generated and said electrical current flow of said electrodes.

4. A process for monitoring biofilm activity on a structure exposed to an aqueous solution as recited in claim 1 wherein the step of measuring the current flow through said electrodes further comprises measuring current flow through said electrodes while maintaining a constant DC potential on said electrodes wherein an increase in current flow indicates biofilm activity.

5. A process for monitoring biofilm activity on a structure exposed to an aqueous solution as recited in claim 1 wherein the step of measuring the current generated by said two electrodes further comprises measuring current flow generated by said electrodes after said electrodes are disconnected from said power source.

6. A process for monitoring biofilm activity on a structure exposed to an aqueous solution as recited in claim 1 further comprising the step of measuring AC resistance between said electrodes after said electrodes are disconnected from said power source.

7. A process for monitoring biofilm activity on a structure exposed to an aqueous solution comprising the steps of;
   a. submerging two electrodes made from the same electrically conducting material, in said aqueous solution and electrically insulating said electrodes from one another and said structure:
   a. connecting said electrodes to a power source: and
   b. measuring the electrical characteristics of said electrodes by the steps of:
      i. measuring current flow generated by said electrodes after said electrodes are disconnected from said power source;
      ii. measuring current flow through said electrodes while maintaining a constant DC potential on said electrodes; and
      iii. measuring AC resistance between said electrodes after said electrodes are disconnected from said power source; and
   c. determining biofilm activity on said electrodes and insulation between said electrodes by analysis of said electrical characteristics:
   whereby changes in said electrical characteristics indicate biofilm activity on said electrodes and said insulation between said electrodes.

8. A method for monitoring biological activity comprising the steps of:
   a. placing two electrically conducting electrodes made from the same material and electrically insulated from each other and from said structure in said aqueous solution;
   b. applying a DC potential for approximately 10 to 60 minutes per day on said electrodes in an aqueous solution to produce biological activity on said sets of electrodes;
   c. measuring the current flowing through said electrodes:
   d. removing said DC potential from said electrodes; and
   e. measuring a DC current or potential generated by biofilm activity on said sets of electrodes;
   whereby an increase of said generated current or potential indicates an increase of biological activity.

* * * * *